US012758426B2

(12) United States Patent
Teuma et al.

(10) Patent No.: US 12,758,426 B2

(45) Date of Patent: Oct. 13, 2026

(54) SYSTEM ASTIGMATISM USING MULTIPLE PAIRED ARCUATE LASER GENERATED CORNEAL INCISIONS

(71) Applicant: Lensar, Inc., Orlando (FR)

(72) Inventors: Eric Valas Teuma, Orlando, FL (US); Rudolph W. Frey, Winter Park, FL (US); Steven E. Bott, Oviedo, FL (US)

(73) Assignee: Lensar, Inc., Orlando, FL (US)

( * ) Notice: Subject to any disclaimer, the term of this patent is extended or adjusted under 35 U.S.C. 154(b) by 103 days.

(21) Appl. No.: 16/673,898

(22) Filed: Nov. 4, 2019

(65) Prior Publication Data

US 2020/0170840 A1 Jun. 4, 2020

Related U.S. Application Data

(62) Division of application No. 13/427,149, filed on Mar. 22, 2012, now Pat. No. 10,463,541.

(60) Provisional application No. 61/467,592, filed on Mar. 25, 2011.

(51) Int. Cl.
*A61F 9/008* (2006.01)

(52) U.S. Cl.
CPC .. *A61F 9/00827* (2013.01); *A61F 2009/0087* (2013.01); *A61F 2009/00872* (2013.01)

(58) Field of Classification Search
CPC .................. A61F 9/008; A61F 9/00827; A61F 2006/0087; A61F 2006/00872
See application file for complete search history.

(56) References Cited

U.S. PATENT DOCUMENTS 4,538,608 A 9/1985 L'Esperance
4,665,913 A * 5/1987 L'Esperance, Jr. .......................... A61F 9/00804 606/3
4,718,418 A 1/1988 L'Esperance
4,764,930 A 8/1988 Bille
4,901,718 A 2/1990 Bille
4,907,586 A 3/1990 Bille
5,098,426 A 3/1992 Sklar
5,246,435 A 9/1993 Bille
5,355,181 A 10/1994 Ashizaki
5,439,462 A 8/1995 Bille
5,480,396 A 1/1996 Simon
6,004,314 A 12/1999 Wei
6,099,522 A 8/2000 Knopp
6,197,018 B1 3/2001 O'Donnell
6,312,422 B1 11/2001 Dubnack
6,322,556 B1 11/2001 Gwon
6,325,792 B1 12/2001 Swinger
7,655,002 B2 2/2010 Myers
8,262,646 B2 9/2012 Frey
8,382,745 B2 2/2013 Naranjo-Tackman
8,394,084 B2 3/2013 Optimedica
(Continued)

*Primary Examiner* — Boniface N Nganga

(74) *Attorney, Agent, or Firm* — Glen P. Belvis; Belvis Law, LLC.

(57) ABSTRACT

A method for the reduction or elimination of astigmatism in an eye that includes an astigmatism axis, the method including determining an astigmatism axis of an eye and forming a first set of incisions in a cornea of the eye that are bisected by the astigmatism axis. The method including forming a second set of incisions in the cornea that are bisected by the astigmatism axis, wherein the first set of incisions and the second set of incisions reduce or eliminate astigmatism in the eye.

19 Claims, 6 Drawing Sheets

(56) References Cited

U.S. PATENT DOCUMENTS

| | | | | |
|---|---|---|---|---|
| 8,403,921 | B2 | 3/2013 | Optimedica | |
| 8,425,497 | B2 | 4/2013 | Optimedica | |
| 8,465,478 | B2 | 6/2013 | Frey | |
| 8,480,659 | B2 | 7/2013 | Frey | |
| 8,500,723 | B2 | 8/2013 | Frey | |
| 8,617,146 | B2 | 12/2013 | Frey | |
| 8,758,332 | B2 | 6/2014 | Frey | |
| 8,801,186 | B2 | 8/2014 | Frey | |
| 9,180,051 | B2 | 11/2015 | Frey | |
| 9,271,645 | B2 | 3/2016 | Frey | |
| 9,375,349 | B2 | 6/2016 | Frey | |
| 9,545,338 | B2 | 1/2017 | Frey | |
| 9,968,485 | B2 | 5/2018 | Potter | |
| 10,213,340 | B2 | 2/2019 | Gray | |
| 10,463,541 | B2 * | 11/2019 | Frey | A61F 9/00827 |
| 10,709,610 | B2 | 7/2020 | Morley | |
| 11,090,190 | B2 | 8/2021 | Morley | |
| 2002/0049437 | A1 * | 4/2002 | Silvestrini | A61B 18/14<br>606/49 |
| 2002/0103478 | A1 | 8/2002 | Gwon | |
| 2007/0173794 | A1 | 7/2007 | Frey | |
| 2007/0185475 | A1 | 8/2007 | Frey | |
| 2008/0287928 | A1 | 11/2008 | Arnoldussen | |
| 2010/0004641 | A1 | 1/2010 | Frey | |
| 2011/0040293 | A1 * | 2/2011 | Bor | A61F 9/008<br>606/5 |
| 2011/0190739 | A1 | 8/2011 | Frey | |
| 2012/0016350 | A1 | 1/2012 | Myers | |
| 2016/0095752 | A1 | 4/2016 | Srinivasan | |
| 2016/0302971 | A1 | 10/2016 | Frey | |
| 2017/0290703 | A1 | 10/2017 | Teuma | |
| 2018/0085256 | A1 | 3/2018 | Gray | |

* cited by examiner

SYSTEM ASTIGMATISM USING MULTIPLE PAIRED ARCUATE LASER GENERATED CORNEAL INCISIONS

This application is a divisional of U.S. Ser. No. 13/427,149 filed Mar. 22, 2012, which claims the benefits of priority under 35 U.S.C. § 119(e)(1) of U.S. Provisional Application Ser. No. 61/467,592, filed Mar. 25, 2011, the entire contents of each of which is incorporated herein by reference.

BACKGROUND OF THE INVENTION

Field of the Invention

The present invention relates to methods and systems for improving surgical procedures for correcting astigmatism.

Discussion of Related Art

A common method of surgically correcting astigmatism is the method of forming limbal relaxing incisions (LRIs) in the eye. As shown in FIG. 1, such LRIs 100 are generally paired arcuate incisions/cuts formed in the cornea 102 of the eye 104, wherein the LRIs 100 subtend an angle relative to a center 106 of the eye 104 that has a magnitude ranging from between about 20° to about 100°. In the example shown in FIG. 1, the angle is approximately 65°. The incisions 100 are typically formed with a diamond or other blade such that they have a depth that is generally from 80% to 100% of the thickness of the cornea 102 and are within around 0.5 mm to 2 mm of the limbus of the eye. The paired arcuate incisions 100 are diametrically opposed across the cornea 102 and disposed along a steep axis of the cornea. The incisions are made at an angle relative to the scale shown at the perimeter of the eye. This "clock" angle, 20° in FIG. 1, is along the direction of the steep axis of the astigmatism. The other indicated angle, 65° in this case, is the subtended arc angle, which is related to the magnitude of the astigmatism being treated. As shown in FIG. 1, the incisions 100 are bisected by the astigmatism axis 108. The standard depth of the incision is 90% of the thickness of the cornea near the limbus (or, in some cases, to a standard thickness of around 600 μm, which represents a depth of about 90% of an average corneal thickness near the limbus). The incisions can be formed either manually with a blade or automatically using a femtosecond laser. By femtosecond laser is meant a laser with a pulse width of between about 100 fs and 10,000 fs.

The mechanism by which the LRIs 100 reduce or eliminate astigmatism is mediated by the changes in the biomechanical structure of the cornea 102 caused by the incisions 100. In particular, the incisions 100 result in a change in the shape of the corneal surfaces such that there is a flattening of the curvature of the corneal surface along the axis connecting the paired arcuate incisions 100. The particular form and magnitude of curvature of the cornea 102 is a result of an equilibrium achieved between an outward force applied by the pressure inside the eye (intraocular pressure or IOP) and inward forces generated by the restoring force of the stressed collagen fibrils which make up the bulk of the cornea 102. The arcuate incisions 100 cut through the collagen fibrils resulting in a weakening of the cornea 100 in a direction perpendicular to the length of the incision. Such weakening allows for greater strain or lengthening of the intact fibrils just posterior to the incision and consequently results in the flattening of the curvature of the cornea perpendicular to the length of the incision.

Though LRIs are fairly widely used for correction of residual astigmatism, particularly for patients undergoing cataract surgery, the procedure is used for only a relatively small fraction of eligible patients (EyeNet Magazine, article 000506, American Academy of Ophthalmology; Nichamin et al, *Cataract and Refractive Surgery Today*, "Corneal Relaxing Incisions", August, 2009). One reason that the procedure is not more universally utilized is that the results of the procedure in correcting astigmatism are variable (Mingo-Botin et al, Journal of Cataract & Refractive Surgery Volume 36, Issue 10, Pages 1700-1708, October 2010; Walter Bethke, *Review of Ophthalmology*, March 2011). The source of variability of the results, though not fully understood, is likely due in part to several factors, such as: 1) variation in the depth or shape of the incisions (due to limits of dexterity of the surgeon, etc.), 2) patient-to-patient variability in the pattern or arrangement of collagen fibrils in the cornea (causing identical incisions to have different effects for different patients), and 3) long term corneal health being compromised by incisions that cut nearly or completely through the cornea.

Recently, the practice of making the incisions manually with a fixed or variable depth blade is starting to be supplanted by incisions made with a femtosecond laser (Maxine Lipner, EyeWorld, "What's Ahead, Femtosecond technology changing the cataract landscape", 2011-3-24 8:45:27). Such a laser makes incisions by focusing ultrashort laser pulses to a very fine focus, causing a plasma mediated photodisruption of the tissue at the point of focus. An incision is generated by placing a contiguous series of such pulses in a pattern that results in the formation of the desired incision. The combined effect of the pattern of pulses is to cleave the tissue at the targeted plane. Arbitrarily complex incisions patterns can be generated with such lasers. The femtosecond lasers are believed to make incisions of a more accurate and consistent depth and of a curvature that more accurately matches the desired arcuate form of the incision. While use of such a laser addresses the first of the concerns mentioned previously, i.e., variability in the clinical outcomes of LRIs due to imprecise cuts, such uses did not address the other two concerns, i.e., patient-to-patient variability in the pattern or arrangement of collagen fibrils in the cornea, and the comprising of long term corneal health by deep incisions.

SUMMARY

One aspect of the invention regards a method for the reduction or elimination of astigmatism in an eye that includes an astigmatism axis, the method including determining an astigmatism axis of an eye and forming a first set of incisions in a cornea of the eye that are bisected by the astigmatism axis. The method including forming a second set of incisions in the cornea that are bisected by the astigmatism axis, wherein the first set of incisions and the second set of incisions reduce or eliminate astigmatism in the eye.

A second aspect of the present invention regards a system for providing an arcuate shot pattern to an eye for reducing astigmatism induced from cataract therapy, the system including a therapeutic laser for producing a laser beam and optics for guiding the laser beam and directing the laser beam to an eye so that the following are formed: 1) a first set of incisions in a cornea of the eye that are bisected by an astigmatism axis of the eye and 2) a second set of incisions in the cornea that are bisected by the astigmatism axis, wherein the first set of incisions and the second set of incisions reduce or eliminate astigmatism in the eye.

One or more aspects of the present invention provides for reducing the effect of patient-to-patient variability in the pattern of collagen fibrils on the reduction or elimination of astigmatism by a surgical procedure.

One or more aspects of the present invention provides for improving long term corneal health when incisions are formed in a cornea and reducing the variability in the results in surgical procedures for reducing or eliminating astigmatism.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

In general, the present invention relates to a method of reducing or eliminating astigmatism in an eye. The method involves forming multiple incisions in the cornea in the eye. Depending on the complexity of the incisions, the incisions can be formed either manually via a diamond or blade or automatically via a laser system. In the case of a laser system, the laser system in general has a treatment or therapeutic laser, optics for delivering the laser beam from the treatment laser to the eye, and a particular pattern which provides for the placement of treatment laser shots in the cornea to create arcuate area of tissue removal. An example of such a laser system is described in U.S. patent application Ser. No. 12/831,783, the entire contents of which are incorporated herein by reference.

Figure 2A:
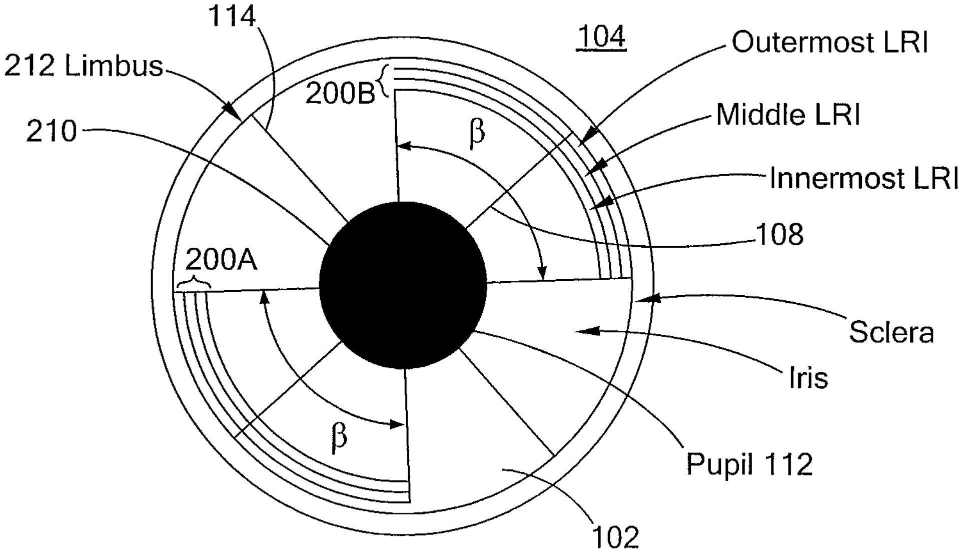
FIG. 2A is a schematic diagram of a first embodiment of arcuate patterns formed in the cornea to reduce or eliminate astigmatism in an eye in accordance with the present invention.
Figure 2B:
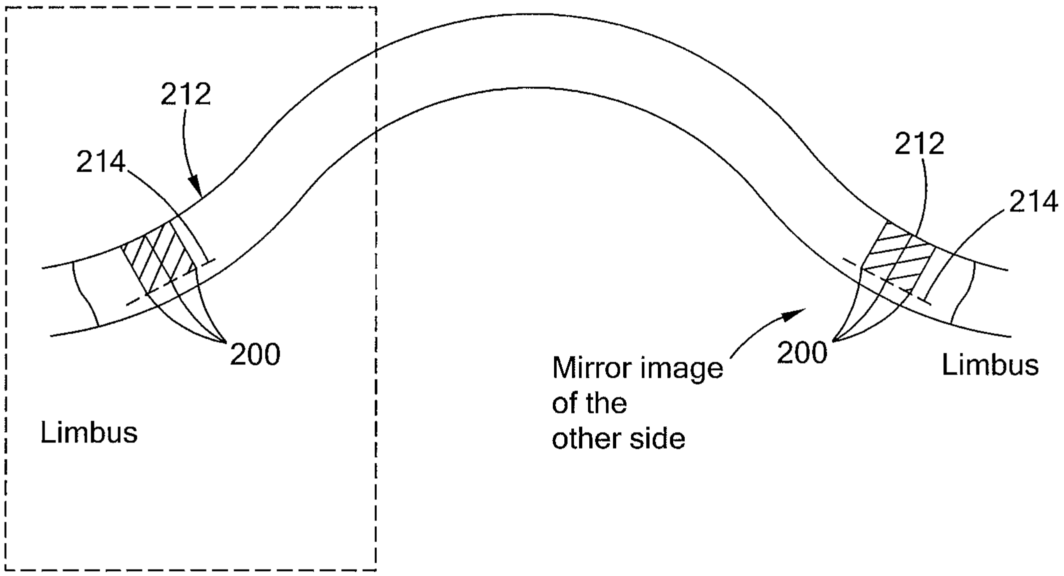
FIG. 2B is a cross-sectional view of a portion of the cornea of FIG. 2A.

An example of an eye 104 surgically treated according to the present invention is shown in FIG. 2A. In particular, two sets of arcuate incisions 200A and 200B are formed in the cornea 102 of the eye 104. The incisions 200A are mirror images with respect to incisions 200B with respect to an axis 114 that is perpendicular to the astigmatism axis 108. Each of the incisions 200A and 200B are formed in a target volume of the cornea defined as being contained in the anterior 90% of the body of the cornea in an annular section of the cornea 102 which is generally located between 0.5 and 3 mm from the limbus. 2A. Each of the incisions is contained in a continuous area that is parallel with the anterior surface of the cornea, which is an exterior surface of the eye. Each incision begins at a first common vertical level 212, which often is the anterior surface of the cornea, and ends at a second common vertical level 214 as shown in FIG. 2B, and where the direction of the incision is generally normal to the surface of the cornea, although the direction of the incisions may also be chosen to be parallel to the axis of the eye or other angles, provided that the residual corneal thickness at the cut is between roughly 10-20% of the corneal thickness near the limbus. As shown in FIG. 2B, the level 214 is generally parallel with the level 212. The target volume is defined by the dashed area between levels 212 and 214. In addition, the incisions 200A and 200B are bisected by the astigmatism axis 108.

Each of the sets of arcuate incisions 200A and 200B subtends an angle β that ranges from 20° to 100° as measured from the center 106 of the pupil 112. As shown in FIG. 2A, there are three incisions in each set of incisions. Each incision has a depth of approximately equal magnitude that ranges from 40% to 80% of the thickness of the cornea. In the example of FIGS. 2A-B, the depth is 60% of the thickness of the cornea. Furthermore, within each particular set of incisions, adjoining incisions are separated from one another by a distance ranging from 0.25 mm to 1 mm. The incisions in each set that are furthest from the pupil are a distance of approximately 0.25 mm to 0.5 mm from the limbus 212.

Figure 1:
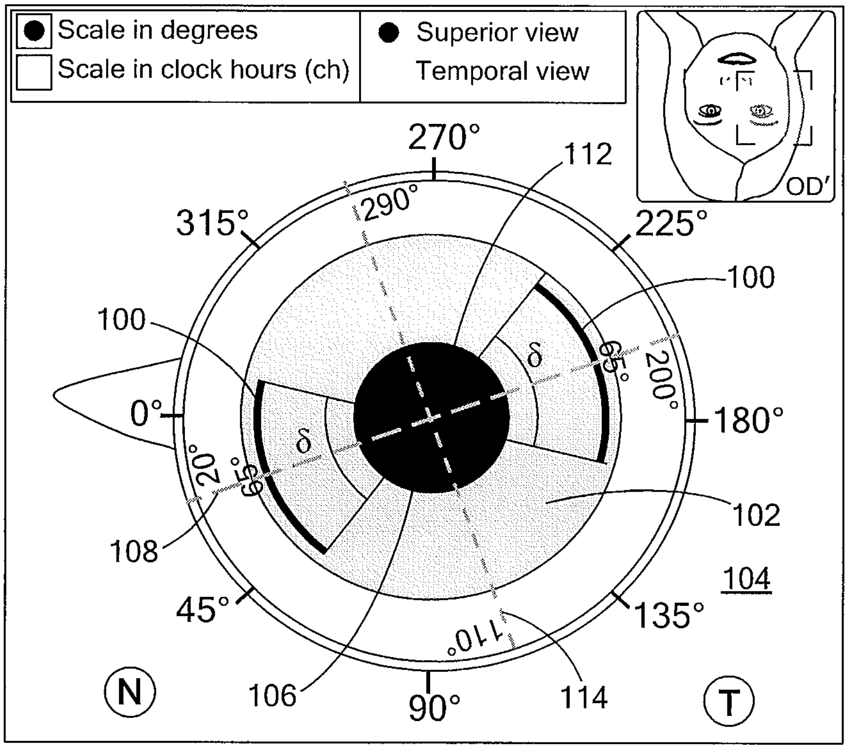
FIG. 1 Prior Art
FIG. 1 is a picture describing a known surgical procedure to reduce or eliminate astigmatism in an eye.
Figure 3:
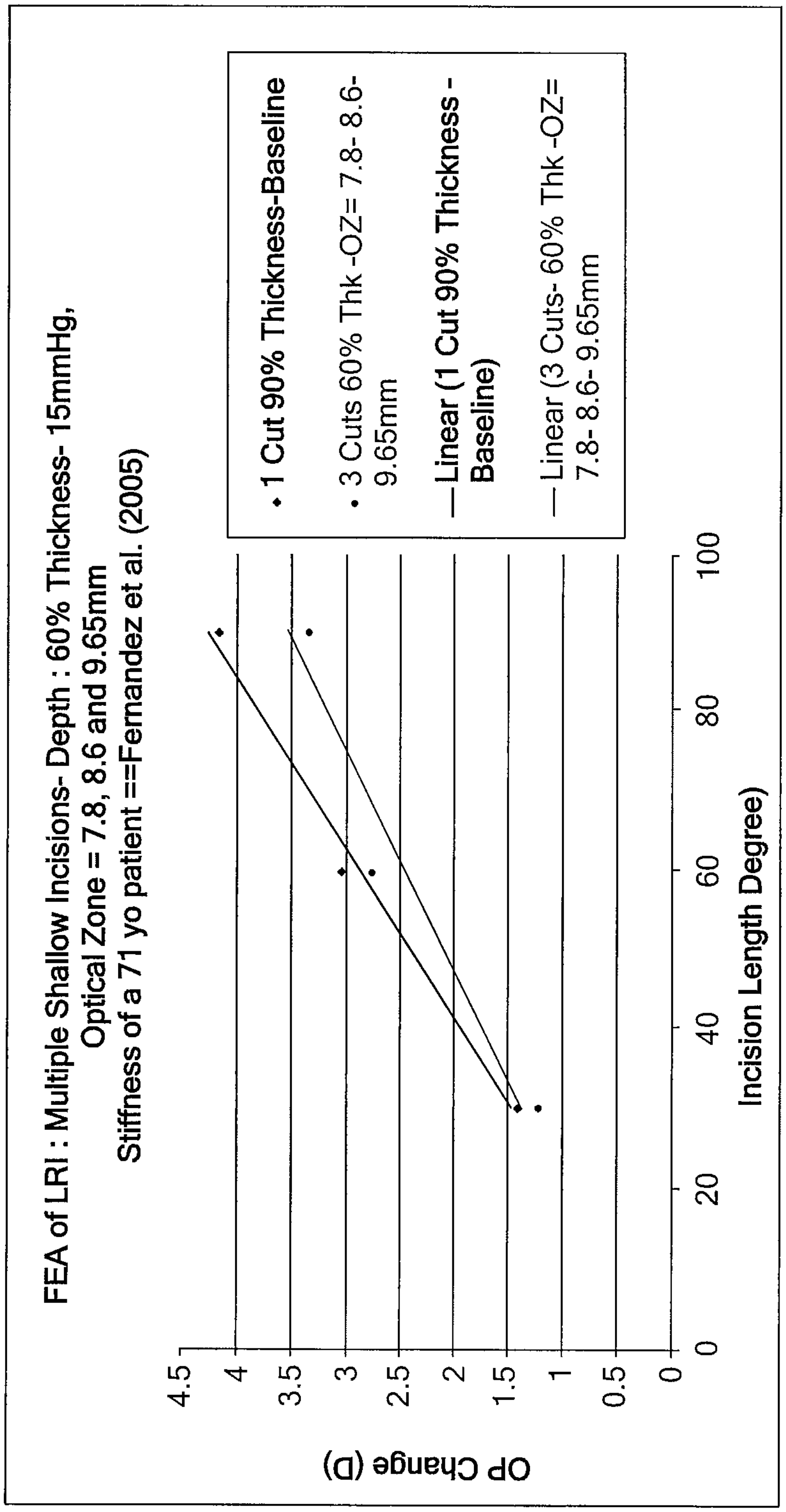
FIG. 3 shows a chart that compares the magnitude of astigmatism correction of arcuate patterns, based on finite element analysis (FEA) modeling of the cornea, formed in accordance with the present invention shown in FIG. 2 with the surgical procedure shown in FIG. 1.

As shown by the chart of FIG. 3, when each set of incisions contains three incisions and are at a depth of 60% of the thickness of the cornea, with a subtended arc of 90°, the astigmatism correction is 90% of the astigmatism correction generated by two single incisions similar to those shown in FIG. 1, wherein each incision has a depth of 90% of the thickness of the cornea.

Note that each set of incisions can contain two, three or more incisions. In the case of two incisions in a set that are at a depth of 60% of the thickness of the cornea, the astigmatism correction is 60% of the astigmatism correction generated by two single incisions similar to those shown in FIG. 1, wherein each incision has a depth of 90% of the thickness of the cornea. This is illustrated in FIG. 3.

In summary, the multiple, concentric pairs of relatively shallow sets of incisions generate a desired astigmatism correction while leaving a much thicker, and therefore more structurally sound cornea than results from conventional 90% thickness incisions.

Figure 4A:
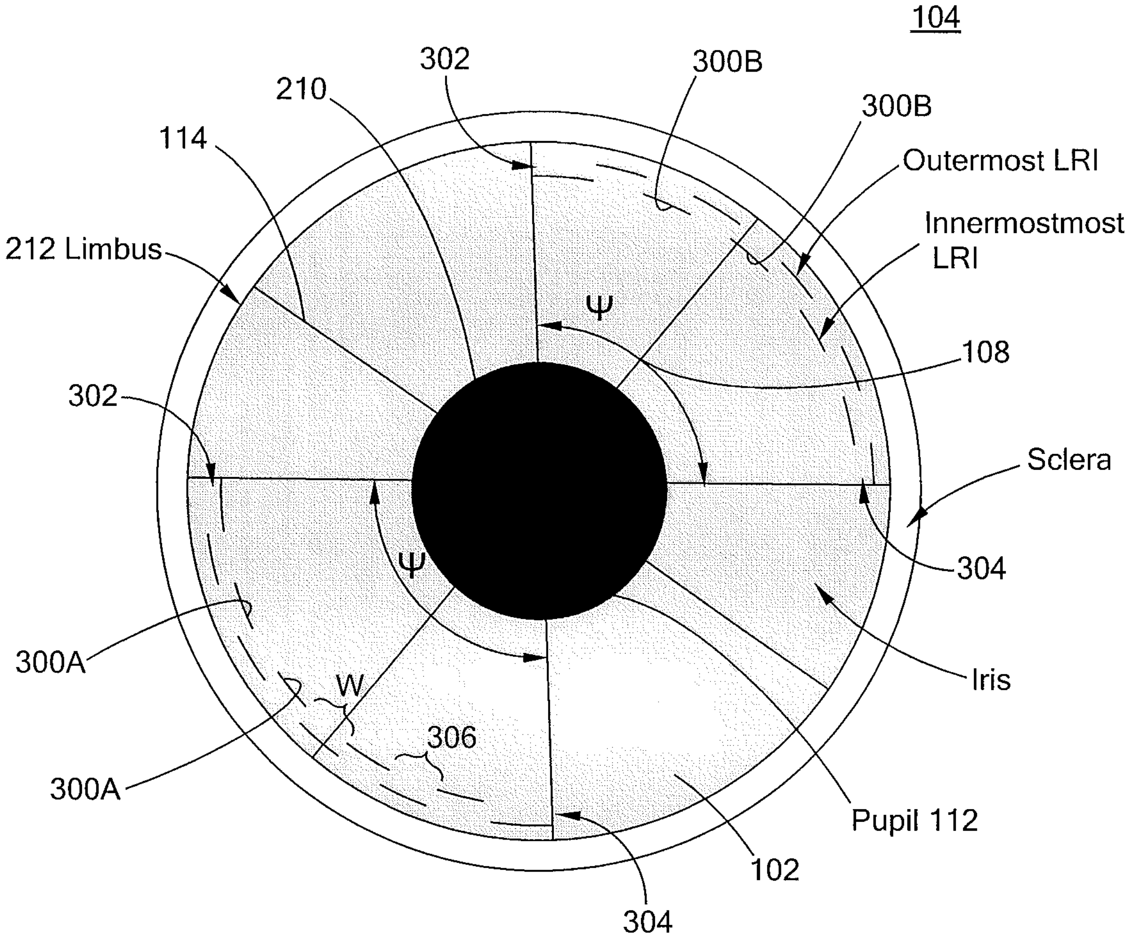
FIG. 4A is a schematic diagram of a second embodiment of arcuate patterns formed in the cornea to reduce or eliminate astigmatism in an eye in accordance with the present invention.

As shown in FIG. 4A, an alternative to multiple, concentric pairs of relatively shallow LRIs 200A, 200 B as shown in FIG. 2 is the use of multiple, concentric pairs of discontinuous LRIs 300A, 300B ("dashed LRIs") with each segment of each incision cut to a depth of about 90% of the thickness of the cornea. When compared with the continuous incisions 200A and B of FIGS. 2A-B, the magnitude of the depth of the cut for a discontinuous LRI 300A, B will be greater. It is believed that the reason for a greater depth of cut is that fewer corneal fibers are cut with discontinuous incisions when compared with LRIs 200A, B. This is compensated for by increasing the depth of the incisions for the discontinuous LRIs.

Figure 4B:
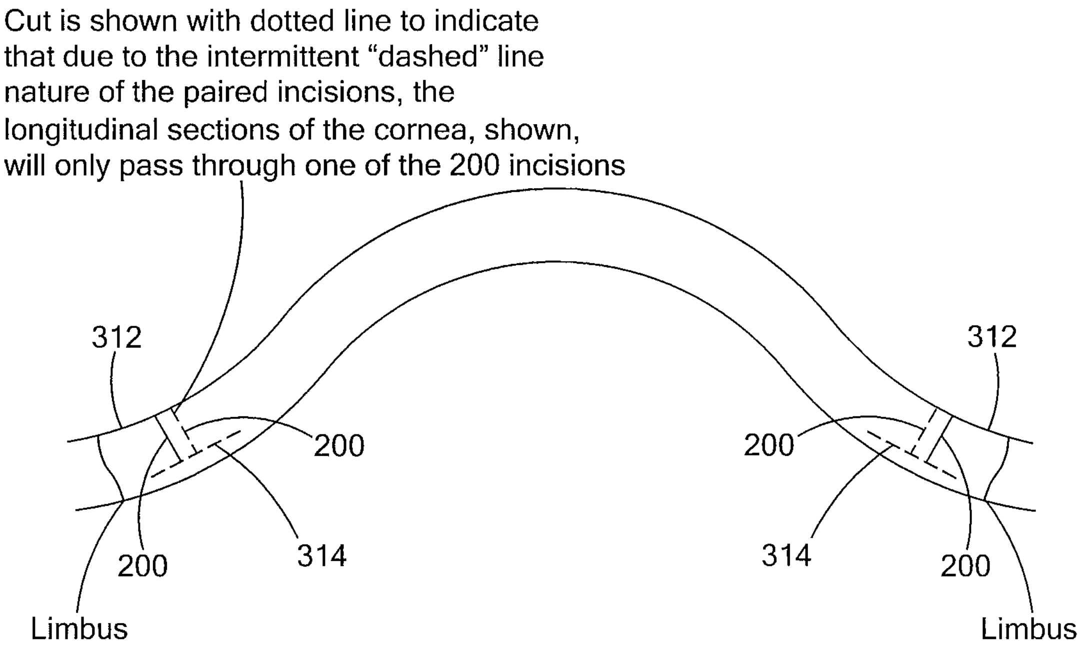
FIG. 4B is a cross-sectional view of a portion of the cornea of FIG. 4A.

The LRIs 300A, 300B can be thought of as having the incisions constrained to be on parallel arcs or lines 302, 304, wherein there are multiple incisions on each arc. Each of the arcs or lines is contained in a common continuous area that is parallel with the anterior surface of the cornea, which is an exterior surface of the eye. Adjoining incisions in a particular arc are separated from one another by gaps 306 having a width W of 0.25 mm to 2 mm and have a similar length as the gap. As shown in FIG. 4A, the gaps 306 of one arc may overlap incisions of an adjoining arc. However, the length of the incisions and gaps within a particular arc may vary over a considerable range while still achieving the same effect. In a manner similar to that shown in FIG. 2B, each of the incisions in each arc begins at a first common vertical level 312 and ends at a second common vertical level 314 as shown in FIG. 4B. Furthermore, the incisions have a depth of approximately 80%-90% of the thickness of the cornea and subtend an angle ψ of approximately 20° to 100°. Note that incisions of one arc present in the cross-sectional plane shown in FIG. 4B are denoted by a solid line while incisions of a parallel arc that are not in the cross-sectional plane of FIG. 4B are denoted by dashed lines.

The incisions shown in FIGS. 4A-B cannot be cut with a manual blade technique because of the intermittent nature of the incisions; however, such incisions can be readily made with a femtosecond laser. The pattern of the incisions preserves structural integrity because of the intermittent nature of the cut and the contiguous band of uncut corneal tissue that winds back and forth across the dashed line segmental incisions. Note that the incisions are staggered to allow the foregoing effect. However, the tensile stress on the collagen fibrils in the cornea, generated by the IOP of the eye, causes the intact fibrils below the incisions to strain or lengthen to much the same extent as with the conventional single pair of complete arcuate incisions. Thus the effect of reducing the curvature of the cornea in the direction perpendicular to the incision (and thus reducing astigmatism) occurs to a similar magnitude as with the conventional LRIs, but with less damage to the structure of the cornea.

The staggering of two or more pairs of dashed LRIs also causes an averaging effect which reduces outcome variability due to the effects of local orientation of the fibrils within the cornea. As mentioned above, variations in the local orientation of the collagen fibrils in the cornea in the area of the incision cause variability in the effect of the cut from patient to patient, even if the cuts are made with identical depth and arcuate shape. The staggering of two or more pairs of dashed LRIs in effect "samples" a larger region of the cornea permitting an averaging of the quasi randomly oriented collagen fibrils over a larger area, thus reducing variability in the amount of change in cornea curvature and correction of astigmatism. The arrangement of collagen fibrils over the cornea as a whole has a generally organized structure with statistically preferred orientations for fibrils located in various regions of the cornea. This large scale organization provides cornea strength and a generally uniform thickness to the cornea, however, the local orientations of individual fibrils within different small regions within the cornea is quasi random (Nigel Fullwood, "Fibril Orientation and Corneal Curvature", *Structure*, Volume 12(2), pp 169-170, February, 2004; Richard H. Newton and Keith M. Meek, "The integration of the corneal and limbal fibrils in the human eye", Biophysical Journal, volume 75, pp 2508-2512 November, 1998). The dashed LRIs thus also address both the second and third of the three factors above which are preventing wider adoption of the use of LRIs.

Figure 5:
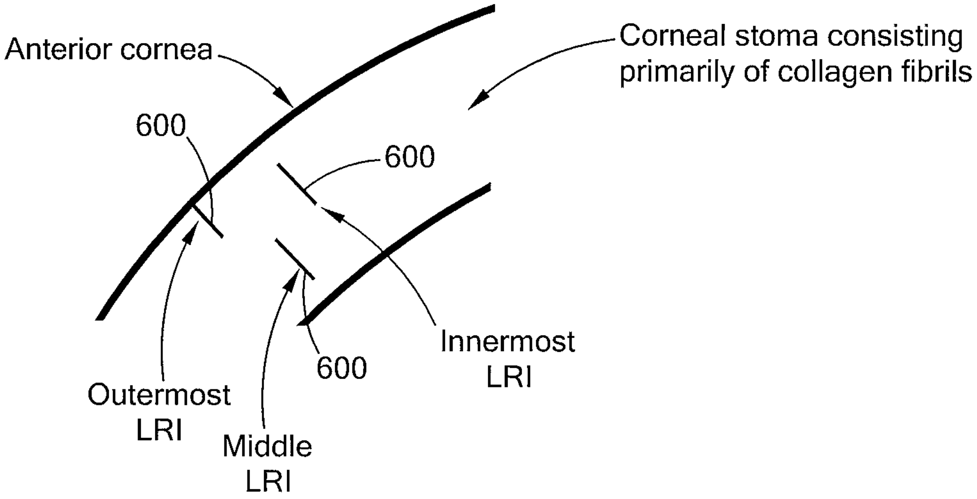
FIG. 5 is a schematic diagram of a third embodiment of arcuate patterns formed in the cornea to reduce or eliminate astigmatism in an eye in accordance with the present invention.

A second alternative approach is illustrated in FIG. 5, wherein a cross section of the cornea near the limbus is shown. In this case, the multiple, concentric paired arcuate incisions 600 are staggered vertically across the depth of the cornea, with each arcuate incision having a depth of 30-60% of the thickness of the cornea. Stated another way, the outermost (relative to the center of the eye) LRI of FIG. 5 is contained in a first continuous area that is parallel with the anterior surface of the cornea, wherein the anterior surface is an exterior surface of the eye. The innermost LRI is contained in a second continuous area that is parallel to the first continuous area and that is further from the anterior surface of the cornea. The middle LRI is even deeper in the cornea and is contained in a continuous area that is parallel to the first and second continuous areas. The continuous areas can be visualized as follows, in terms of shells of an onion. First the onion is cut in half, lengthwise and most of the inner shells are removed, leaving just the three outermost shells. The first and second continuous areas are like the outermost and next to outermost shell of an onion. The middle LRI is cut in the innermost of the three outermost onion shells. (Since only one side of the cornea is shown, the corresponding set of incisions diametrically across the cornea is not shown.) In the case of three pairs of incisions as described with respect to FIG. 5, the incisions in each arc are continuous and so will appear so from above in a manner similar to that shown in FIG. 2A. The effect of the vertically staggered multiple paired incisions is similar to the dashed LRIs: a similar magnitude of astigmatism correction is possible with less compromise to the structural integrity of the cornea, due to the staggering of the individual, shallower incisions. As with the dashed LRIs, the vertically staggered LRIs in effect "sample" a larger region of the cornea permitting an averaging of the quasi randomly oriented collagen fibrils over a larger area, thus reducing variability in the amount of change in cornea curvature and correction of astigmatism.

[In the embodiment of FIG. 5, the depth for each cut for the various LRI's has a magnitude that ranges from about 200 μm to about 400 μm, wherein the depth of cut for the outermost, middle, and innermost LRIs can have identical or differing magnitudes. In addition, the spacing between one level of cuts, such as the outermost LRI, and an adjacent level of cuts, such as the middle LRI, is about 0.25 mm to about 1 mm. Also, the different levels of cuts can be found at depths from the surface ranging from 0 μm to about 400 μm. The angle subtended by each level of cuts is the same as described with the embodiment in FIG. 2. The set of incisions should together span a vertical depth of 80% to 90% of the depth of the cornea at the limbus.

Note that while the previous descriptions regarded one of continuous rings, discontinuous rings or staggered rings, it is contemplated that the goals of the present invention could be achieved by a combination two or more of the embodiments of FIGS. 2, 4 and 5.

Figure 6:
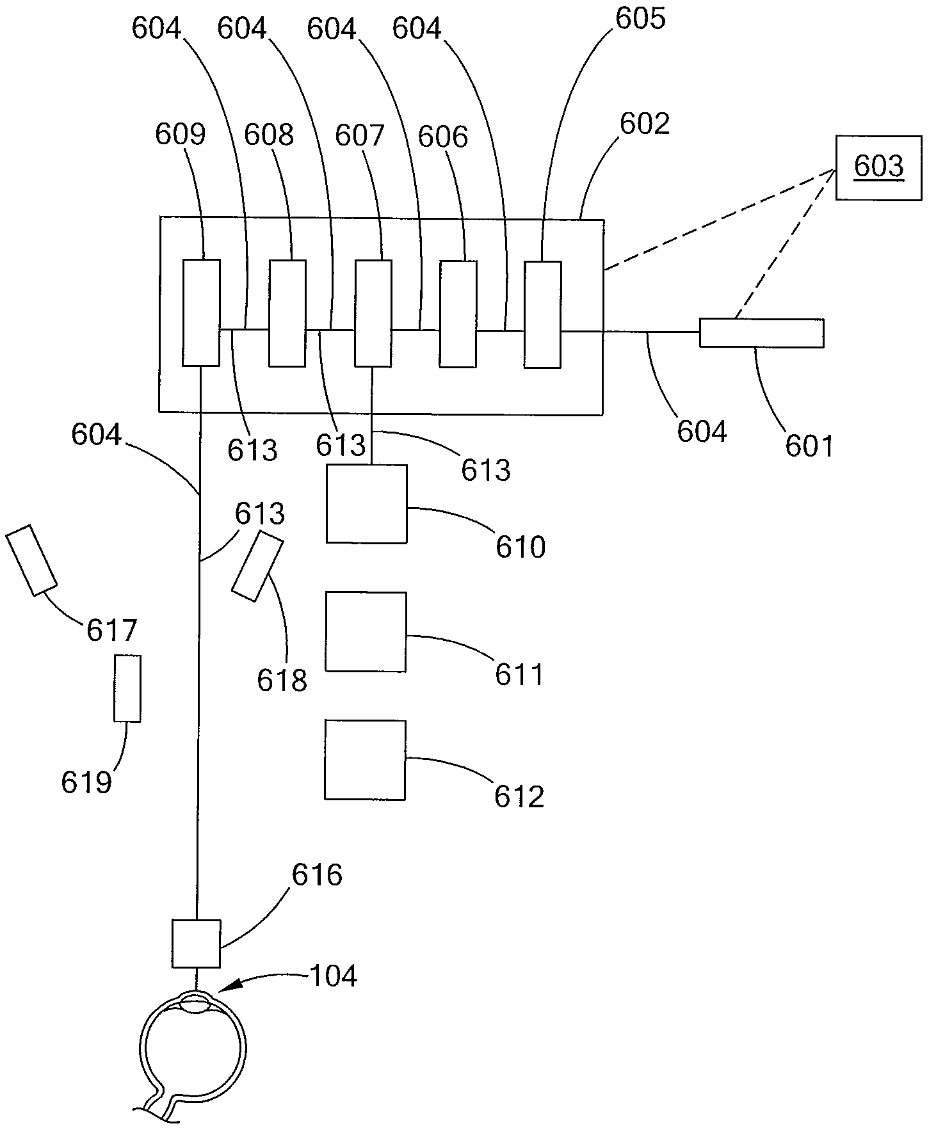
FIG. 6 is a block diagram of a femtosecond laser system which could be used to generate LRIs as described herein.

In order to form the arcuate patterns of FIGS. 2-5, a laser system is provided as shown in FIG. 6 and as described in U.S. patent application Ser. No. 12/831,783, the entire contents of which are incorporated herein by reference. In particular, the laser system includes a treatment laser 601 which should provide a beam 604. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser, with accompanying shock wave and cavitation bubble. The term photodisruption has also been generally referred to as Laser Induced Optical Breakdown (LIOB). In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in U.S. Patent Application Publication No. 2007/084694 A2 and WO 2007/084627A2, the entire contents of each of which are incorporated herein by reference. These and other similar lasers may be used as therapeutic lasers. For procedures on the cornea the same type of therapeutic laser as described herein may be used, with the energy and focal point being selected to perform the desired procedure.

In general, the optics 602 for delivering the laser beam 604 to the structures of the eye should be capable of providing a series of shots to the natural lens in a precise and predetermined pattern in the x, y and z dimension. The z dimension as used herein refers to that dimension which has an axis that corresponds to, or is essentially parallel with the anterior to posterior (AP) axis of the eye. The optics should also provide a predetermined beam spot size to cause photodisruption with the laser energy reaching the structure of the eye intended to be cut.

In general, the control system 603 for delivering the laser beam 604 may be any computer, controller, and/or software hardware combination that is capable of selecting and controlling x-y-z scanning parameters and laser firing. These components may typically be associated at least in part with circuit boards that interface to the x-y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser and/or from a separate controller for the slit scanned laser system.

The laser optics 602 for delivering the laser beam 104 includes a beam expander telescope 605, a z focus mechanism 606, a beam combiner 607, an x-y scanner 608, and focusing optics 609. There is further provided relay optics 610, camera optics 611, which include a zoom, and a first ccd camera 612.

Optical images of the eye 614 and in particular optical images of the natural lens 615 of the eye 104 are conveyed along a path 613. This path 613 follows the same path as the laser beam 604 from the natural lens through the laser patient interface 616, the focusing optics 609, the x-y scanner 608 and the beam combiner 607. There is further provided a laser patient interface 616, a structured light source 617 and a structured light camera 618, including a lens. The structured light source may alternatively be deployed along the same path as the laser beam. Examples of patient interface and related apparatus that are useful with the present system are provided in regular and provisional U.S. patent application Ser. No. 12/509,021 and Ser. No. 61/228,457 wherein the entire disclosures of each of which are incorporated herein by reference.

The structured light source 617 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5, which is also referred to as a slit scanned laser. In this embodiment the structured illumination source 617 also includes slit scanning means 619.

When using a scanned slit illumination the operation includes positioning the slit on one side of the lens, taking an image then moving the slit approximately one slit width, then taking another image, and then repeating this sequence until the entire lens is observed. For example, a 100 μm slit width can scan a nominal 9 mm dilated pupil diameter in 90 images, which takes approximately 3 seconds using a 30 Hz frame rate camera. To obtain images of the anterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

The structured light illumination source 617 and the structured light camera 118 are arranged in an angled relationship. The angled relationship may be but is not required to be in the so-called Scheimpflug configuration, which is well-known. The structured light source 617, in conjunction with the slit scanning means 619, projects a line and or a plurality of lines onto the eye lens 615 at an angle or plurality of angles. The light scattered at the eye lens 615 forms the object to be imaged by the lens and focused onto the camera system 618. Since the slit illuminated image in the eye lens 615 may be at a large angle with respect to the camera 618, this presents a large depth of field to the camera and the entire slit image may not be in sharp focus at the camera. By tilting the camera at an angle or plurality of angles the image along the illuminated plane can be in sharper focus. To the extent that a sharper focus is not obtained, arithmetic data evaluation means are further provided herein to determine a more precise location of the illuminated structures with respect to the laser device.

The images from the camera 618 may be conveyed to the controller 603 for processing and further use in the operation of the system. They may also be sent to a separate processor and/or controller, which in turn communicates with the controller 603. The structured light source 617, the camera 618 and the slit scanning means 619 include a means for determining the position and apex of the lens in relation to the laser system.

Other systems for measuring the position of the cornea could be used instead of the slit laser, Scheimpflug camera system described above, An example of an OCT (optical coherence tomography) based system for guiding an ophthalmic laser is US 2009/0131921. Any such system could be used in the current invention.

Note that alternative structures can be used to form the arcuate patterns of FIGS. 2-5, such as the laser systems described in U.S. Provisional Patent Application Ser. No. 61/455,178 and U.S. Patent Application Publication No. 2010/0022995, the entire contents of each of which is incorporated herein by reference. In addition, an alternative to the structured light source and Scheimpflug camera described above with respect to the embodiment shown in FIG. 6 would be an optical coherence tomographer (OCT) which in a slightly different way performs the same function of accurately measuring the positions and shapes of ocular structures within the eye (particularly the anterior and posterior cornea and lens surfaces) within a laser-defined x,y,z coordinate system to allow the correct placement of laser incisions within the cornea and lens.

From the foregoing description, one skilled in the art can readily ascertain the essential characteristics of this invention, and without departing from the spirit and scope thereof, can make various changes and/or modifications of the invention to adapt it to various usages and conditions.

We claim:

1. A system for providing arcuate shot patterns to an eye for reducing astigmatism induced from cataract therapy, the system comprising:

a) a therapeutic laser for producing a laser beam;

b) a control system configured to maintain data and perform calculations; wherein the control system is configured to deliver the laser beam to the eye in a predetermined first arcuate shot pattern configured to provide a first set of arcuate incisions in a cornea of the eye and a predetermined second arcuate shot pattern configured to provide a second set of arcuate incisions in the cornea;

c) the control system comprising an induced astigmatism axis for the eye; and, d) the control system configured to control optics for guiding the laser beam and directing the laser beam to the eye, based at least in part upon the induced astigmatism axis, so that the following are formed: the first set of arcuate incisions in the cornea that cut across and are bisected by the induced astigmatism axis of the eye and configured and positioned on the cornea to reduce or eliminate an induced astigmatism in the eye; and the second set of arcuate incisions in the cornea that cut across and are bisected by the induced astigmatism axis and configured and positioned on the cornea to reduce or eliminate the induced astigmatism in the eye;

e) wherein at least one incision of the first set of acuate incisions has a start point at a surface of the cornea and an end point within the cornea at a first vertical level, and at least one of the second set of arcuate incisions has a start point at the surface of the cornea and an end point within the cornea at a second vertical level; a distance between the surface of the cornea and the first vertical level thereby defining a depth of the at least one of the first set of arcuate incisions, and a distance between the surface of the cornea and the second vertical level thereby defining a depth of the at least one of the second set of arcuate incisions; and the depth of the at least one of the first set of arcuate incision and the at least one of the second set of arcuate incisions ranging from 40% to 80% of the thickness of the cornea.

2. The system of claim 1, wherein the first set of arcuate incisions comprises a first continuous incision and a second continuous incision, wherein each of the first continuous incision and the second continuous incision subtend a common angle with respect to a center of the eye.

3. The system of claim 2, wherein the second set of arcuate incisions comprises a third continuous incision and a fourth continuous incision, wherein each of the third continuous incision and the fourth continuous incision subtend a second common angle with respect to a center of the eye, wherein the common angle and the second common angle are equal in magnitude.

4. The system of claim 3, wherein the first continuous incision and the second continuous incision are contained within a continuous area that is parallel to an exterior surface of the eye.

5. The system of claim 4, wherein the third continuous incision and the fourth continuous incision are contained within the continuous area.

6. The system of claim 3, wherein the first continuous incision is contained within a first continuous area that is parallel to an exterior surface of the eye and the second continuous incision is contained within a second continuous area that is parallel to the first continuous area.

7. The system of claim 4, wherein the third continuous incision is contained within a first continuous area and the fourth continuous incision is contained within a second continuous area.

8. The system of claim 1, wherein the first set of arcuate incisions is substantially a mirror image of the second set of arcuate incisions with respect to an axis perpendicular to the astigmatism axis.

9. The system of claim 8, wherein the first set of arcuate incisions is comprises a first continuous incision and a second continuous incision, wherein each of the first continuous incision and the second continuous incision subtend a common angle with respect to a center of the eye.

10. The system of claim 9, wherein the second set of arcuate incisions comprises a third continuous incision and a fourth continuous incision, wherein each of the third continuous incision and the fourth continuous incision subtend a second common angle with respect to a center of the eye, wherein the common angle and the second common angle are equal in magnitude.

11. The system of claim 10, wherein the first continuous incision and the second continuous incision are contained within a continuous area that is parallel to an exterior surface of the eye.

12. The system of claim 11, wherein the third continuous incision and the fourth continuous incision are contained within the continuous area.

13. The system of claim 10, wherein the first continuous incision is contained within a first continuous area that is parallel to an exterior surface of the eye and the second continuous incision is contained within a second continuous area that is parallel to the first continuous area.

14. The system of claim 13, wherein the third continuous incision is contained within the first continuous area and the fourth continuous incision is contained within the second continuous area.

15. The system of claim 1, wherein the first set of arcuate incisions comprises a first set of spaced cuts lying along a first arcuate line and a second set of spaced cuts along a second arcuate line, wherein each of the first arcuate line and the second arcuate line subtend a common angle with respect to a center of the eye.

16. The system of claim 15, wherein the second set of arcuate incisions comprises a third set of spaced cuts lying along a third arcuate line and a fourth set of spaced cuts lying along a fourth arcuate line, wherein each of the third arcuate line and the fourth arcuate line subtend a second common angle with respect to a center of the eye, wherein the common angle and the second common angle are equal in magnitude.

17. The system of claim 1, wherein the first set of arcuate incisions comprises a first continuous incision and a second continuous incision, wherein the first continuous incision is contained within a first continuous area that is parallel to an exterior surface of the eye and the second continuous incision is contained within a second continuous area that is parallel to the first continuous area.

18. The system of claim 17, wherein the second set of arcuate incisions comprises a third continuous incision and a fourth continuous incision, wherein the third continuous incision is contained within the first continuous area and the second continuous incision is contained within the second continuous area.

19. The system of claim 1, wherein the first set of arcuate incisions comprises arcuate first incisions and the second set of arcuate incisions comprises arcuate second incisions.

* * * * *